(12) United States Patent
Nawata et al.

(10) Patent No.: US 8,623,909 B2
(45) Date of Patent: Jan. 7, 2014

(54) PROPHYLACTIC/THERAPEUTIC AGENTS FOR LIFESTYLE-RELATED DISEASES

(75) Inventors: Hajime Nawata, Fukuoka (JP); Toshihiko Yanase, Fukuoka (JP); Takayoshi Nakagawa, Kawasaki (JP)

(73) Assignees: Aska Pharmaceutical Co., Ltd., Tokyo (JP); Hajime Nawata, Fukuoka (JP)

( * ) Notice: Subject to any disclaimer, the term of this patent is extended or adjusted under 35 U.S.C. 154(b) by 222 days.

(21) Appl. No.: 12/991,155

(22) PCT Filed: May 8, 2009

(86) PCT No.: PCT/JP2009/058659
§ 371 (c)(1),
(2), (4) Date: Nov. 5, 2010

(87) PCT Pub. No.: WO2009/136629
PCT Pub. Date: Nov. 12, 2009

(65) Prior Publication Data
US 2011/0104066 A1    May 5, 2011

(30) Foreign Application Priority Data
May 9, 2008   (JP) ................................ 2008-123197

(51) Int. Cl.
*C07D 311/78* (2006.01)
*A61K 31/35* (2006.01)

(52) U.S. Cl.
USPC ............................. 514/453; 549/384; 435/6.1

(58) Field of Classification Search
None
See application file for complete search history.

(56) References Cited

U.S. PATENT DOCUMENTS

| 5,519,051 A * | 5/1996 | Koizumi et al. ............. 514/453 |
| 2002/0058290 A1 | 5/2002 | Ostrowski et al. |
| 2003/0225040 A1 | 12/2003 | Dalton et al. |
| 2005/0107416 A1 | 5/2005 | Dankulich et al. |
| 2008/0139630 A1 | 6/2008 | Hanney et al. |
| 2009/0163588 A1 | 6/2009 | Turnbull et al. |

FOREIGN PATENT DOCUMENTS

JP    2007-211014 A    8/2007

OTHER PUBLICATIONS

Gao et al "Selective Androgen Receptor Modulator Treatment Improves Muscle Strength and Body Composition and Prevents Bone Loss in Orchidectomized Rats" (Endocrinology, 2005: vol. 146, No. 11, pp. 4887-4897.*
Weet et al in "Mineralocorticoid properties of potential metabolites of 18-hydroxydeoxycorticosterone and 18-hydroxyprogesterone" (Journal of Medicinal Chemistry, 1985: vol. 28, pp. 233-239).*
Uyanik et al in "Ring A aromatic steroids in the pregnane series" (Journal of Chemical Research, 2006: vol. 7, No. 1, pp. 417-419).*
Mohler et al in "Nonsteroidal Selective Androgen Receptor Modulators (SARMS): Dissociating the Anabolic and Androgenic Activities of the Androgen Receptor for Therapeutic Benefit" (J. of Medicinal Chemistry, Jun. 25, 2000: vol. 52, No. 12, pp. 3597-3617).*
Mohler et al in "Nonsteroidal Selective Androgen Receptor Modulators (SARMS): Dissociating the Anabolic and Androgenic Activities of the Androgen Receptor for Therapeutic Benefit" (J. of Medicinal Chemistry, Jun. 25, 2009: vol. 52, No. 12, pp. 3597-3617). Note:post-filing date is Jun. 25, 2009. This reference was provided on Dec. 6, 2012.*
Reich et al in "Ergosteroids III. Syntheses and biological activity of seco-steroids related to dehydroepiandrosterone" (Steroids: 1998 vol. 63, No. 10, pp. 542-553).*
Gasi et al in "Synthesis and anti-aromatase activity of some new steroidal D-lactones" (Steroids: 2005 vol. 70, No. 1, pp. 47-53).*
Taiji Tsukamoto et al., "Sentakuteki Androgen Juyotai Modulator (SARM)—Kaihatsu no Genjo to Tenbo-", Clinical Calcium, 2007, vol. 17, No. 9, pp. 120-124.
Kiminobu Goto et al., "Zenritsusen Gan Chiryo ni Mochiirareru Ko-Androgen-zai no Androgen Receptor ni Taisuru Sayo", Pharma Medica, 1999, vol. 17, No. 5, pp. 97 to 103.
Piu, F. et al., Pharmacological characterization of AC-262536, a novel selective androgen receptor modulator, J. Steroid Biochem. Mol. Biol., Mar. 2008, vol. 109. No. 1-2, pp. 129-137.
Noriko Yamamoto et al., "Shinki Sentakuteki Androgen Juyotai Chosetsuzai (SARM) no Hone to Zenritsusen ni Okeru in vitro Narabini in vivo deno Sayo no Hikaku", Dai 25 Kai The annual meeting of the Japanese Society for Bone and Mineral Research: program & abstracts, 2007, psgr 286.
Fan, W. et al., Androgen receptor null male mice develop late-onset obesity caused by decreased energy expenditure and lipolytic activity but show normal insulin sensitivity with high adiponectin secretion., Diabetes, 2005, vol. 54, No. 4, pp. 1000-1008.
Chongqing Sun et al., "Discovery of Potent, Orally-Active, and Muscle-Selective Androgen Receptor Modulators Based on an N-Aryl-hydroxybicyclohydantoin Scaffold," *J. Med. chem.*, 2006, 49, 7596-7599.
Partial English-language translation of pp. 99 to 100 of K. Goto et al., *Pharma Medica*, 1999, vol. 17, No. 5, pp. 97-103 (including the original text pp. 99-100).
Partial English-language translation of N. Yamamoto et al., Dai 25 Kai The annual meeting of the Japanese Society for Bone and Mineral Research: program & abstracts, 2007, p. 286 (including the original text).
English-language International Preliminary Report on Patentability and Written Opinion of the International Searching Authority, dated Dec. 13, 2010 for International Application PCT/JP2009/058659 filed May 8, 2009; Applicants; ASKA Pharmaceutical Co., Ltd et al.

* cited by examiner

*Primary Examiner* — Catherine Hibbert
(74) *Attorney, Agent, or Firm* — Holtz Holtz Goodman & Chick, P.C.

(57) ABSTRACT

Disclosed is a method for screening a compound having an activity that selectively modulates an androgen receptor, comprising a step of measuring the mRNA expression level of prostate-specific antigen or the production level of prostate-specific antigen in prostate cancer cells by contacting a test substance with the prostate cancer cells, and a step of measuring the mRNA expression level of uncoupling protein 1 or the production level of uncoupling protein 1 in adipocytes by contacting a test substance with the adipocytes. Additionally disclosed is a selective androgen receptor modulator, comprising as an active ingredient thereof a compound represented by any of structural formulas (I) to (III), and a composition for preventing or treating a lifestyle-related disease, comprising as an active ingredient thereof said selective androgen receptor modulator.

7 Claims, 2 Drawing Sheets

SEQUENCE LISTING

```
<160> NUMBER OF SEQ ID NOS: 24

<210> SEQ ID NO 1
<211> LENGTH: 15
<212> TYPE: DNA
<213> ORGANISM: Artificial
<220> FEATURE:
<223> OTHER INFORMATION: forward primer

<400> SEQUENCE: 1
cacctgctcg ggtga                                                         15

<210> SEQ ID NO 2
<211> LENGTH: 20
<212> TYPE: DNA
<213> ORGANISM: Artificial
<220> FEATURE:
<223> OTHER INFORMATION: reverse primer

<400> SEQUENCE: 2
ccacttccgg taatgcacca                                                    20

<210> SEQ ID NO 3
<211> LENGTH: 18
<212> TYPE: DNA
<213> ORGANISM: Artificial
<220> FEATURE:
<223> OTHER INFORMATION: forward primer

<400> SEQUENCE: 3
caccttcccg ctggacac                                                      18

<210> SEQ ID NO 4
<211> LENGTH: 25
<212> TYPE: DNA
<213> ORGANISM: Artificial
<220> FEATURE:
<223> OTHER INFORMATION: reverse primer

<400> SEQUENCE: 4
ccctaggaca cctttatacc taatg                                              25

<210> SEQ ID NO 5
<211> LENGTH: 19
<212> TYPE: DNA
<213> ORGANISM: Artificial
<220> FEATURE:
<223> OTHER INFORMATION: forward primer
```

```
<400> SEQUENCE: 5
aaactacctt aactccatc                                                 19

<210> SEQ ID NO 6
<211> LENGTH: 20
<212> TYPE: DNA
<213> ORGANISM: Artificial
<220> FEATURE:
<223> OTHER INFORMATION: reverse primer

<400> SEQUENCE: 6
atgatcttga tcttcattgt                                                20

<210> SEQ ID NO 7
<211> LENGTH: 22
<212> TYPE: DNA
<213> ORGANISM: Artificial
<220> FEATURE:
<223> OTHER INFORMATION: forward primer

<400> SEQUENCE: 7
gcaatgcctg ggtacatggt gg                                             22

<210> SEQ ID NO 8
<211> LENGTH: 24
<212> TYPE: DNA
<213> ORGANISM: Artificial
<220> FEATURE:
<223> OTHER INFORMATION: reverse primer

<400> SEQUENCE: 8
gtcgtaccac aggcattgtg atgg                                           24

<210> SEQ ID NO 9
<211> LENGTH: 24
<212> TYPE: DNA
<213> ORGANISM: Artificial
<220> FEATURE:
<223> OTHER INFORMATION: forward primer

<400> SEQUENCE: 9
aggtgacaga tctcatgctg tgtg                                           24

<210> SEQ ID NO 10
<211> LENGTH: 20
<212> TYPE: DNA
<213> ORGANISM: Artificial
<220> FEATURE:
<223> OTHER INFORMATION: reverse primer

<400> SEQUENCE: 10
tggctggcat attgggttca                                                20

<210> SEQ ID NO 11
<211> LENGTH: 22
<212> TYPE: DNA
<213> ORGANISM: Artificial
<220> FEATURE:
<223> OTHER INFORMATION: forward primer

<400> SEQUENCE: 11
cccaagttcg agtttgctgt ca                                             22
```

<210> SEQ ID NO 12
<211> LENGTH: 19
<212> TYPE: DNA
<213> ORGANISM: Artificial
<220> FEATURE:
<223> OTHER INFORMATION: reverse primer

<400> SEQUENCE: 12
tccacctgtg gcacgttca					19

<210> SEQ ID NO 13
<211> LENGTH: 22
<212> TYPE: DNA
<213> ORGANISM: Artificial
<220> FEATURE:
<223> OTHER INFORMATION: forward primer

<400> SEQUENCE: 13
ggcacagtca aggctgagaa tg					22

<210> SEQ ID NO 14
<211> LENGTH: 21
<212> TYPE: DNA
<213> ORGANISM: Artificial
<220> FEATURE:
<223> OTHER INFORMATION: reverse primer

<400> SEQUENCE: 14
atggtggtga agacgccagt a					21

<210> SEQ ID NO 15
<211> LENGTH: 14
<212> TYPE: DNA
<213> ORGANISM: Artificial
<220> FEATURE:
<223> OTHER INFORMATION: forward primer

<400> SEQUENCE: 15
gcgcggacga cgga					14

<210> SEQ ID NO 16
<211> LENGTH: 25
<212> TYPE: DNA
<213> ORGANISM: Artificial
<220> FEATURE:
<223> OTHER INFORMATION: reverse primer

<400> SEQUENCE: 16
agtcactgtc ttggttgttg atgag					25

<210> SEQ ID NO 17
<211> LENGTH: 17
<212> TYPE: DNA
<213> ORGANISM: Artificial
<220> FEATURE:
<223> OTHER INFORMATION: forward primer

<400> SEQUENCE: 17
gcgggcgtgg taatgct					17

<210> SEQ ID NO 18
<211> LENGTH: 21
<212> TYPE: DNA
<213> ORGANISM: Artificial

```
<220> FEATURE:
<223> OTHER INFORMATION: reverse primer

<400> SEQUENCE: 18
ctgttcgcaa atacgctcca t                                          21

<210> SEQ ID NO 19
<211> LENGTH: 20
<212> TYPE: DNA
<213> ORGANISM: Artificial
<220> FEATURE:
<223> OTHER INFORMATION: forward primer

<400> SEQUENCE: 19
attttggcga cagactcagg                                            20

<210> SEQ ID NO 20
<211> LENGTH: 20
<212> TYPE: DNA
<213> ORGANISM: Artificial
<220> FEATURE:
<223> OTHER INFORMATION: reverse primer

<400> SEQUENCE: 20
aggggcagga atcaaacaag                                            20

<210> SEQ ID NO 21
<211> LENGTH: 20
<212> TYPE: DNA
<213> ORGANISM: Artificial
<220> FEATURE:
<223> OTHER INFORMATION: forward primer

<400> SEQUENCE: 21
tgagaccaag tggcatcgtt                                            20

<210> SEQ ID NO 22
<211> LENGTH: 21
<212> TYPE: DNA
<213> ORGANISM: Artificial
<220> FEATURE:
<223> OTHER INFORMATION: reverse primer

<400> SEQUENCE: 22
ctcttgggct cagtgggtag a                                          21

<210> SEQ ID NO 23
<211> LENGTH: 21
<212> TYPE: DNA
<213> ORGANISM: Artificial
<220> FEATURE:
<223> OTHER INFORMATION: forward primer

<400> SEQUENCE: 23
tacccagctg tgcaatgacc a                                          21

<210> SEQ ID NO 24
<211> LENGTH: 23
<212> TYPE: DNA
<213> ORGANISM: Artificial
<220> FEATURE:
<223> OTHER INFORMATION: reverse primer

<400> SEQUENCE: 24
gcacacaaac atgatgacgt tcc                                        23
```

PROPHYLACTIC/THERAPEUTIC AGENTS FOR LIFESTYLE-RELATED DISEASES

This application is the United States national phase application of International Application PCT/JP2009/058659 filed May 8, 2009.

TECHNICAL FIELD

The present invention relates to a selective androgen receptor modulator (SARM) comprising as an active ingredient thereof a compound that demonstrates androgenic activity on adipocytes, bone, muscle and the like without stimulating the prostate gland.

BACKGROUND ART

Androgens demonstrate the various functions in the promotion of sexual differentiation and the induction of male phenotype. In males, the high active endogenous androgens in mediating these functions are testosterone (T) and 5α-dihydrotestosterone (DHT).

Plasma T levels decline linearly and progressively in men with aging at the rate of about 1% per year starting from their early twenties (Metabolism, 46, 410-413; J. Clin. Endocrinol. Metab., 86, 724-731; J. Clin. Endocrinol. Metab., 87, 589-598). This decline in the bioavailable T is thought to be associated with changes in a body fat distribution, diminished energy expenditure, diminished muscle strength and bone density, diminished physical function, reduced sexual function and depressed mood (J. Gerontol., 57A, M76-M99; Endocrine Rev., 26, 833-876; Med. Hypoth., 60, 448-452; J. Alzheimer's Dis., 5, 267-269; Cell. Mol. Life Sci., 62, 281-292). This androgen-deficient state in the aging males is often called andropause or late-onset hypogonadism (LOH). Androgen therapy, using an injectable, oral, and more recently, transdermal preparation, has been used for many years for the various male disorders. Several clinical studies have shown that the supplementation of T at physiologic doses in the elderly men results in a significant increase in a lean body mass, a decrease in adipose tissue, and an increase in muscle strength and bone density (J. Clin. Endocrinol. Metab., 84, 2647-2653; Am. J. Physiol. Endocrinol. Metab., 282, E601-E607; J. Am. Med. Assoc., 288, 2282-2292; Am. J. Physiol. Endocrinol. Metab., 284, E120-E128; J. Clin. Endocrinol. Metab., 90, 678-688; J. Clin. Endocrinol. Metab., 90, 1502-1510).

However, testosterone (T) replacement therapy in the elderly males is often limited due to concerns over potential side effects including a hyperstimulation of the prostate, increased hematocrit, liver dysfunction and sleep apnea syndrome (Am. J. Med., 110, 563-572; J. Am. Geriat. Soc., 51, 101-115; N. Engl. J. Med., 350, 482-492; J. Clin. Endocrinol. Metab., 89, 4789-4796; Ann. Rev. Med., 56, 117-137). In particular, there is concern over hyperstimulation of the prostate leading to occult, subclinical benign prostate hypertrophy (BPH) or prostate cancer. Consequently, it is extremely important to develop compounds having a distinct tissue specificity corresponding to a particular disease. Such a compound is referred to as a selective androgen receptor modulator (SARM) (J. Clin. Endocrinol. Metab., 84, 3459-3462), and this compound has the potential to maintain or improve the muscle strength and muscle function, prevent the osteoporosis and/or fractures by increasing the bone density, demonstrate the anti-obesity activity, demonstrate the anti-diabetic activity and/or anti-hyperlipemic activity by improving the insulin sensitivity, demonstrate the anti-dementia activity and improve the libido and sexual function in the elderly men in particular without the concomitant deleterious effects on the prostate, liver or erythrocytes that are commonly associated with the steroid treatment regimens.

Androgen receptors (AR) are the transcription factors that are also the members of the family of nuclear receptors. AR are widely distributed in the reproductive and non-reproductive tissues, including the prostate gland and seminal vesicles, male and female external genitalia, testes, ovaries, skin, cardiac muscle, skeletal muscle, liver, and brain cortical or subcortical regions. Despite this wide-ranging distribution of AR, natural ligands in the form of dihydrotestosterone and synthetic AR ligands demonstrate the different activities. This is because the types and concentrations of cofactors (co-activators or co-repressors) present within the cell nuclei differ depending to the type of each tissue or cell, and as a result of the differences in the complex formation occurring due to the co-activator or co-repressor binding, AR are able to selectively control the individual genes in the specific tissues. Recently, the details of a transcription control mechanism of a complex consisting of a ligand-nuclear receptor formed by binding with a ligand, and a co-activator or co-repressor have been elucidated. If the structure of the ligand differs, then the three-dimensional structure of the ligand-nuclear receptor complex also differs, which in turn also results in the differences in binding to a co-activator or co-repressor. Thus, since SARMs have the specific, partial agonistic activity that induces the various forms of transcription control in the different tissues and cells, they are expected to lead to the development of novel therapeutic drugs having the unique activity profiles.

Compounds that do not act on the prostate but exhibit the activities on the muscle or bone have previously been reported that were developed starting from the known AR antagonists bicalutamide and flutamide (J. Med. Chem., 49, 7596-7599). Various other compounds are also known to be SARMs (for example, Japanese Unexamined Patent Publication No. 2007-211024, Japanese Translation of PCT International Application Publication No. 2007-526336, Japanese Translation of PCT International Application Publication No. 2008-501800). Although the activities of SARMs are used for the various purposes, for example, in the case of the elderly men suffering from osteopenia or osteoporosis, if the target site is the bone of those men, a more anabolic SARM with a clear activity on the bone and muscle, but a lesser activity on the prostate and other sex accessory organs is desired.

DISCLOSURE OF THE INVENTION

An object of the present invention is to provide a screening method for finding a compound that demonstrates an androgenic activity on a tissue other than the prostate gland without stimulating the prostate gland. In addition, another object of the present invention is to provide an SARM that comprises as an active ingredient thereof a compound that demonstrates an androgenic activity on the tissue other than the prostate gland without stimulating the prostate gland. Moreover, still another object of the present invention is to provide a composition for preventing or treating the lifestyle-related diseases that comprises this SARM.

The inventors of the present invention first screened a compound that does not stimulate the expression level of prostate-specific antigen (PSA) of prostate cancer cells in order to find a compound having SARM activities among the numerous synthetic AR ligands and dehydroepiandrosterone (DHEA) derivatives. Next, uncoupling protein 1 (UCP-1), which is related to an energy consumption and lipid metabolism, was selected as a second screening marker. UCP-1 uncouples an energy substrate oxidation from a mitochondrial ATP production, and as a result thereof, brings about the consumption of thermal energy which is thought to reduce a body weight (J. Appl. Physiol., 92, 2187-2198). The inventors of the present invention previously found that, in an androgen receptor knockout (ARKO) male mice, an expression of UCP-1 mRNA decreased considerably, and the late-onset obesity caused by inhibition of an energy consumption was demonstrated, and that DHT-AR has a direct stimulatory activity on the expression of UCP-1 (Diabetes, 54, 1000-1008). On the basis of these findings, UCP-1 expression activity was tested for test compounds as a secondary screening. As a result, several compounds having a beneficial effect on the lipid metabolism were able to be found.

Moreover, these compounds were also examined for the presence of additional activities by measuring the changes in the prostate weight, the expression levels of the prostate-specific antigen mRNA or the production levels of the prostate-specific antigen in the prostate, the changes in weight of the anal levator muscle, the changes in the femoral bone density, the changes in the vertebral bone density, the changes in the plasma gonadotropin levels, the changes in the plasma adiponectin levels, the changes in the plasma insulin levels, the changes in the plasma triglyceride levels, the changes in the plasma cholesterol levels, mRNA expression levels of sterol regulatory element binding protein 1 in the liver and visceral fat, mRNA expression levels of carnitine palmitoyl transferase 1 in visceral fat, mRNA expression levels of fatty acid synthases in the liver and visceral fat, and the changes in the body weight, the bone mineral density, the fat distribution, the amount of exercise, the serum glucose concentration and the serum insulin concentration when given a high-fat diet.

Thus, according to the present invention, a method is provided for screening the compounds that have a selective androgen receptor modulatory activity, characterized in comprising the following steps:

(1) a step of adding a test substance to a cultured prostate cancer cell, and measuring the mRNA expression level of prostate-specific antigen (PSA) or the production level of prostate-specific antigen (PSA) in said cultured prostate cancer cell; and, (2) a step of adding a test substance to a cultured adipocyte, and measuring the mRNA expression level of uncoupling protein 1 (UCP-1) or the production level of uncoupling protein 1 (UCP-1) in said cultured adipocytes;

the method further comprises at least one of the following steps in addition to the steps (1) and (2) above:

(a) a step of administering a test substance to a castrated animal, and measuring a change in prostate weight of said animal, (b) a step of administering a test substance to a castrated animal, and measuring a mRNA expression level of prostate-specific antigen or a production level of prostate-specific antigen in a prostate gland of said animal, (c) a step of administrating a test substance to a castrated animal, and measuring a change in weight of anal levator muscle of said animal, (d) a step of administering a test substance to a castrated animal, and measuring a change in femoral bone density of said animal, (e) a step of administering a test substance to a castrated animal, and measuring a change in vertebral bone density of said animal, (f) a step of administering a test substance to a castrated animal, and measuring a change in plasma gonadotropin level of said animal, (g) a step of administering a test substance to a castrated animal, and measuring a change in plasma adiponectin level of said animal, (h) a step of administering a test substance to a castrated animal, and measuring a change in plasma insulin level of said animal, (i) a step of administering a test substance to a castrated animal, and measuring a change in plasma triglyceride level of said animal, (j) a step of administering a test substance to a castrated animal, and measuring a change in plasma cholesterol level of said animal, (k) a step of administrating a test substance to a castrated animal, and measuring mRNA expression level of sterol regulatory element binding protein 1c in the liver and visceral fat of said animal, (l) a step of administering a test substance to a castrated animal, and measuring mRNA expression level of carnitine palmitoyl transferase 1 in the liver and visceral fat of said animal, (m) a step of administrating a test substance to a castrated animal, and measuring mRNA expression level of fatty acid synthase in the liver and visceral fat of said animal, and (n) a step of administering a test substance and a high-fat diet to a test animal, and measuring at least one change selected among body weight, bone mineral density, fat distribution, amount of exercise, serum glucose concentration and serum insulin concentration of said animal.

Moreover, the present invention also includes a selective androgen receptor modulator that comprises as an active ingredient thereof a compound having a selective androgen receptor modulatory activity obtained according to the aforementioned screening method of (1) and (2) or the aforementioned screening method in which at least one step of steps (a) to (n) is added to (1) and (2).

In addition, according to the present invention, a selective androgen receptor modulator is provided that comprises as an active ingredient thereof a compound represented by any of the following formulas (I) to (III):

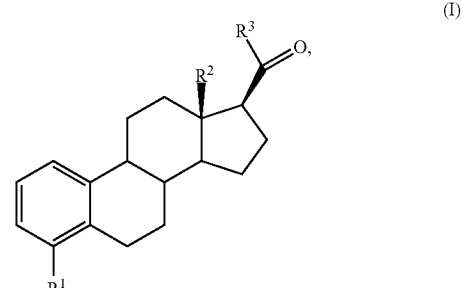

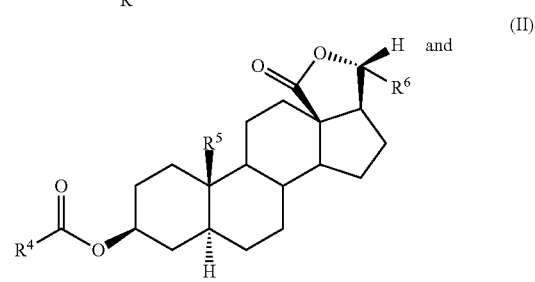

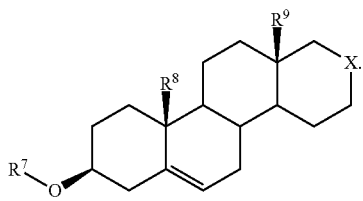

(wherein, $R^1$ to $R^9$ respectively and independently represent a hydrogen atom or $C_{1-4}$ alkyl group, and X represents an oxygen atom or sulfur atom), and a selective androgen receptor modulator is provided that comprises as an active ingredient thereof a compound represented by any of the following formulas (Ia) to (IIIa):

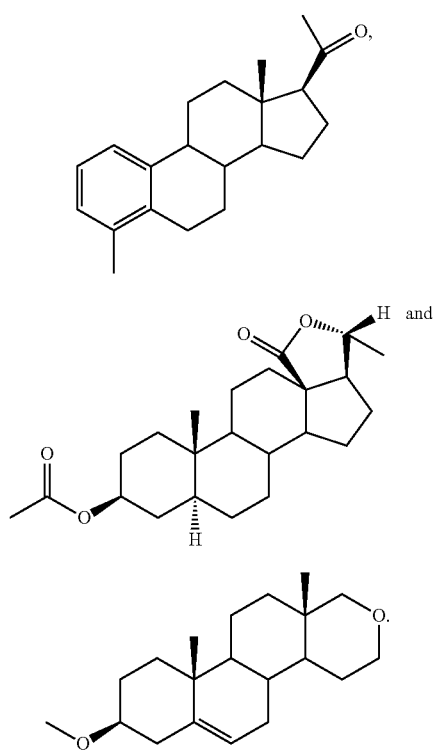

According to the present invention, a composition for preventing or treating a lifestyle-related disease, characterized in comprising a selective androgen receptor modulator comprising as an active ingredient thereof a compound having a selective androgen receptor modulatory activity obtained according to the screening method of the present invention, a compound represented by any of the aforementioned formulas (I) to (III), or a compound represented by any of the aforementioned formulas (Ia) to (IIIa), and further a composition for preventing or treating a lifestyle-related disease wherein the lifestyle-related disease is at least one disease selected from the group consisting of obesity, insulin-resistant (type 2) diabetes, hyperlipemia and hypertension, are provided.

Moreover, according to the present invention, a method for preventing or treating a lifestyle-related disease is provided by administering to a human a selective androgen receptor modulator comprising as an active ingredient thereof a compound having selective androgen receptor modulatory activity obtained according to the screening method of the present invention, a compound represented by the aforementioned formulas (I) to (III), or a compound represented by the aforementioned formulas (Ia) to (IIIa). In particular, the prostate gland is not affected in a preferable embodiment of the prophylactic or therapeutic method of the present invention.

Moreover, according to the present invention, a compound represented by the following formula:

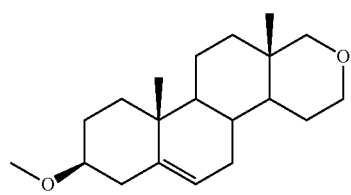

is provided.

BEST MODE FOR CARRYING OUT THE INVENTION

Figure 1:
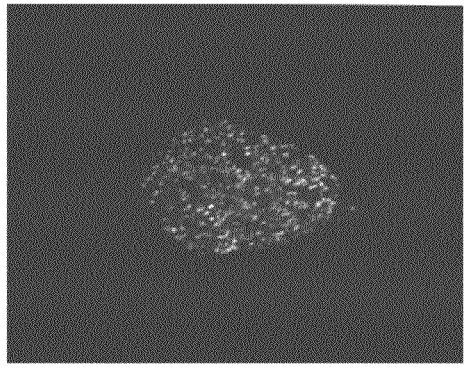
FIG. 1 is an image of an LNCaP cell transfected with AR-GFP followed by treatment with $10^{-7}$ M dihydrotestosterone as observed with a confocal laser fluorescence microscope.

In the present description, the word "selective" in the phrase "selective androgen receptor modulator" refers to having several desirable activities but not having several undesirable activities among any activities possessed by androgen in the body. Thus, in the selective androgen receptor modulator of the present invention, examples of desirable activities include an activity that enhances the mRNA expression level of uncoupling protein 1 or enhances the production level of uncoupling protein 1 in adipocytes, an activity that increases the muscle weight, an activity that increases the bone density, an activity that enhances the insulin sensitivity, an activity that lowers the plasma triglyceride levels, an activity that increases the mRNA expression level of carnitine palmitoyl transferase 1 in the liver and/or visceral fat, and an activity that reduces the prostate weight, and a plurality of these desirable activities can be possessed. In addition, examples of the undesirable activities of the selective androgen receptor modulator of the present invention include an activity that enhances the mRNA expression level of the prostate-specific antigen or the production level of the prostate-specific antigen in the prostate cancer cells, an activity that enhances the mRNA expression level of the prostate-specific antigen or the production level of the prostate-specific antigen in the prostate tissue, an activity that increases the prostate weight, an activity that increases the plasma gonadotropin levels, an activity that increases the plasma and/or serum insulin levels, an activity that elevates the mRNA expression level of the sterol regulatory element binding protein 1 in the liver and/or visceral fat, an activity that elevates the mRNA expression level of the fatty acid synthase in the liver and/or visceral fat, an activity that increases the body weight, an activity that increases the visceral fat, and an activity that elevates the serum glucose concentration. Here, although the selective androgen receptor modulator of the present invention may have several undesirable activities, it preferably at least does not possess the activity of enhancing the mRNA expression level of the prostate-specific antigen or the production level of the prostate-specific antigen in the prostate cancer cells. Moreover, the term "modulator" in the phrase "selective androgen receptor modulator" also includes the case of not having any activities in addition to an agonistic activity and antagonistic activity.

Lifestyle-related diseases are defined as "a group of diseases in which lifestyle factors such as eating habits, exercise habits, recreation, smoking and alcohol consumption are involved in the onset and progression thereof", and include diseases such as obesity, insulin-resistant (type 2) diabetes, hyperlipemia (excluding familial hyperlipemia), hypertension, hyperuricemia, cardiovascular disease (excluding congenital cardiovascular diseases), colorectal cancer (excluding familial colorectal cancer), pulmonary squamous cell carcinoma, chronic bronchitis, emphysema, alcoholic liver disease, osteoporosis or periodontitis. Among these diseases, the selective androgen receptor modulator of the present invention is particularly effective for the prevention or treatment of obesity, insulin-resistant (type 2) diabetes, hyperlipemia and hypertension.

The compound represented by formula (Ia) is described in, for example, Journal of Chemical Research, 7, 417-419 (2006), and the compound of formula (I) can be easily produced according to the production method described therein. In addition, the compound of formula (IIa) is described in, for example, Journal of Medicinal Chemistry, 28, 233-239 (1985), and the compound of formula (II) can be easily produced according to the production method described therein. Although the compound of formula (IIIa) is a novel compound, it can be easily produced according to a method as described in the following method (a), namely by methylating a hydroxyl group in the compound of the following formula (IIIb). Example 1 to be described below may be referred to for the information on details such as the reaction conditions. Furthermore, the compound of formula (IIIb), which is the starting substance in the following method (a), is described in, for example, Production Example 29 of International Patent Publication WO 92/17489, and the compound of formula (III) can be easily produced according to the production method described in said publication.

Method (a):

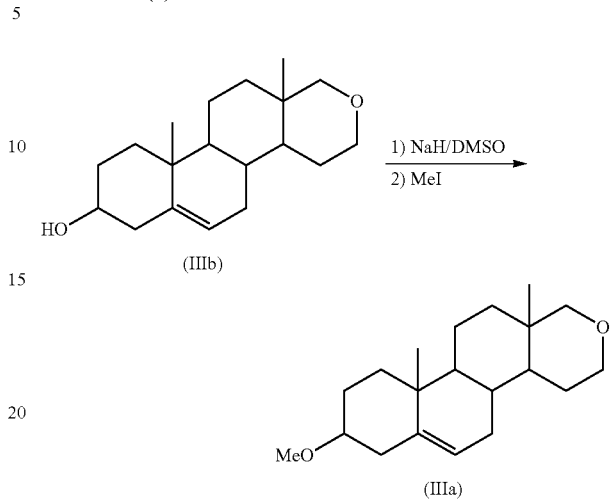

The effect on LNCaP cells, the effect on NIH-3T3-L1 cells and the effect on the various tissues by a compound having a selective androgen receptor modulatory activity obtained according to the screening method of the present invention, particularly a compound of the aforementioned formulas (Ia) to (IIIa), can be demonstrated with the experiments described below.

(1) Measurement of Transcription Activity:
1) Plasmid Construction

Plasmid pCMV-hAR was constructed based on a method previously reported by the inventors of the present invention (J. Biol. Chem., 282, 7329-7338). In addition, reporter plasmids consisting of PGL3-PSA (human) and PGL3-UCP-1 (mouse) were also constructed based on a method previously reported by the inventors of the present invention (Diabetes, 54, 1000-1008). Furthermore, pRL-SV40 was acquired commercially.

2) Cell Culturing

NIH-3T30-L1 mouse preadipocytes were cultured in Dulbecco's modified Eagle's medium (Sera Laboratories) containing 10% fetal calf serum. In addition, cells of human prostate cancer cell line LNCap were cultured in RPMI 1640 medium (Sigma) containing 10% fetal calf serum. Furthermore, these two types of cell lines were obtained from the American Type Culture Collection (Manassas).

3) Transfection

The NIH-3T3-L1 cells of 2) above were co-transfected with pCMV-hAR, pRL-SV40 and PGL3-UCP-1 (mouse) in a 24-well plate using an Effectene Transfection Kit (Qiagen) and a Fugene HD Kit (Roche Diagnostics). In addition, the LNCaP cells of 2) above were similarly co-transfected with pCMV-hAR, pRL-SV40 and PGL3-PSA (human).

4) Measurement of Effect on PSA Promoter-Luciferase Activity in LNCaP Cells

The LNCaP cells co-transfected in 3) above were cultured for 24 hours in DMEM or RPMI 1640 containing 10% fetal calf serum treated with dextran-charcoal and a test compound (dissolved in a small amount of DMSO) 24 hours after transfection. Subsequently, the activities of firefly luciferase and Renilla luciferase were assayed in a 24-well plate using the Dual-Luciferase Reporter Assay System (Promega) in accordance with the protocol of Minilumat LB9507 (Berthold Technologies). The values of each test compound relative to PSA promoter-luciferase activity are shown in the following Table 1. Furthermore, the value of firefly luciferase activity were normalized based on the internal Renilla control, and were presented as relative luciferase activity.

TABLE 1

Value of Luciferase Transcription Activity of Test Compounds

| Test Compound | Concentration | Activity |
|---|---|---|
| Control (DMSO) | 0.1% | 1.0 |
| Dihydrotestosterone | $10^{-7}$ M | 9.4 |
|  | $10^{-8}$ M | 9.7 |
| Compound of formula (Ia) | $10^{-5}$ M | 1.3 |
| Compound of formula (IIa) | $10^{-5}$ M | 0.8 |
| Compound of formula (IIIa) | $10^{-5}$ M | 0.8 |

As shown in Table 1 above, although PSA promoter activity is stimulated roughly 9-fold by dihydrotestosterone at $10^{-7}$ M or $10^{-8}$ M, the compounds of formulas (Ia) to (IIIa) hardly caused any increase in PSA promoter activity.

(2) Measurement of Intracellular mRNA Expression Levels:

1) Extraction of Total RNA

After respectively culturing the LNCaP cells and NIH-3T3-L1 cells co-transfected in 1) to 3) above in 6-well plates, the cells were cultured for 24 hours in EMEM or RPMI 1640 containing 10% fetal calf serum treated with dextran-charcoal and a test compound (dissolved in a small amount of DMSO). Subsequently, total RNA was respectively extracted using Isogen (Wako Pure Chemical Industries).

2) Real-Time PCR

5 µg aliquots of each total RNA obtained in 1) above were reverse-transcribed to first strand cDNA using a Superscript III Kit (Invitrogen) and brought to a final volume of 20 µL. Real-time PCR was carried out using LightCycler FastStart DNA Master SYBR Green I (Roche Diagnostic) in order to quantify expression of PSA mRNA in LNCaP cells and UCP-1 mRNA in NIH-3T3-L1 cells. PCR was carried out under the following conditions in 20 µL of reaction mixture: 50 cycles consisting of denaturing for 3 seconds at 95° C., annealing for 10 seconds at 60° C. and elongating for 25 seconds at 72° C. β-actin mRNA was also simultaneously amplified for use as an internal standard. The sequences of the forward and reverse primers for each of the target transcription products are shown in the following Table 2. Real-time PCR value for each transcription product were calculated as a relative ratio to β-actin.

TABLE 2

Sequences of Primers for Human PSA and Mouse UCP-1

| Target | Forward | Reverse | Size (bp) |
|---|---|---|---|
| Human PSA | CACCTGCT CGGGTGA (SEQ ID NO: 1) | CCACTTCCGG TAATGCACCA (SEQ ID NO: 2) | 150 |
| Mouse UCP-1 | CACCTTCCC GCTGGACAC (SEQ ID NO: 3) | CCCTAGGACACCT TTATACCTAATG (SEQ ID NO: 4) | 91 |
| Human β-actin | AAACTACCTT AACTCCATC (SEQ ID NO: 5) | ATGATCTTGA TCTTCATTGT (SEQ ID NO: 6) |  |

TABLE 2-continued

Sequences of Primers for Human PSA and Mouse UCP-1

| Target | Forward | Reverse | Size (bp) |
|---|---|---|---|
| Mouse β-actin | GCAATGCCTGG GTACATGGTGG (SEQ ID NO: 7) | GTCGTACCACAG GCATTGTGATGG (SEQ ID NO: 8) | 492 |

3) mRNA Expression Levels

Expression levels of PSA mRNA in LNCaP cells and UCP-1 mRNA in NIH-3T3-L1 cells are shown in the following Table 3.

TABLE 3 mRNA Expression Levels of Target Compounds (relative ratios to β-actin mRNA)

| Test Compound | Concentration | PSA mRNA | UCP-1 mRNA |
|---|---|---|---|
| Control (DMSO) | 0.1% | 1.0 | 1.0 |
| Dihydrotestosterone | $10^{-7}$M | 2.5* | 2.0* |
| Compound of formula (Ia) | $10^{-5}$M | 0.8 | 2.1* |
| Compound of formula (IIa) | $10^{-5}$M | 0.9 | 1.4 |
| Compound of formula (IIIa) | $10^{-5}$M | 0.8 | 1.8 |

*$p < 0.05$ (vs. DMSO)

According to Table 3 above, the compounds of formulas (Ia) to (IIIa) were determined to increase UCP-1 mRNA levels relating to an energy consumption without having an effect on PSA mRNA levels.

(3) Study on Subnuclear Localization of GFP-AR:

The ligand-induced formation of subnuclear foci (dots) was determined to be intimately involved with the transcription activation function of subnuclear receptors based on a study previously conducted by the inventors of the present invention (Diabetes, 54, 1000-1008; J. Med. Chem., 49, 7596-7599; J. Biol. Chem., 276, 28395-28401; Mol. Endocrinol., 16, 694-706; Mol. Endocrinol., 18, 127-141). Dihydrotestosterone induces the formation of 250 to 400 fine, distinctly separated subnuclear AR foci (dots), and co-activators such as steroid receptor co-activator 1 (SRC-1), TIF-2 and CBP (CREB-binding protein) are mobilized. Although AR binds to anti-androgen such as hydroxyflutamide, since they do not form foci (dots), the formation of clear foci (dots) by steroid hormone receptors to which an agonist has bound within the nucleus is an indicator of transcription activity. Subnuclear localization of GFP (green fluorescence protein)-AR was examined with respect to the compound of formula (Ia).

NIH-3T3-L1 cells and LNCaP cells were cultured in 35 mm glass dishes (2×$10^5$ cells/dish, Asahi Techno Glass) and transfected with hAR-GFP plasmid at a rate of 2 µg/dish using a Fugene HD Kit (Roche Diagnostics). After culturing for 24 hours, the cells were treated with dihydrotestosterone or the compound of formula (Ia), and observed 3 hours later using an LSM 510 META Microscope (Carl Zeiss).

Figure 2:
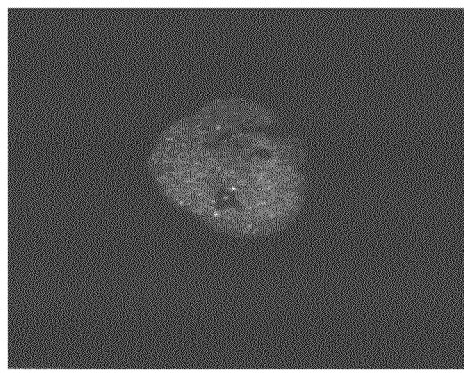
FIG. 2 is an image of an LNCaP cell transfected with AR-GFP followed by treatment with a compound represented by formula (I) at $10^{-5}$ M as observed with a confocal laser fluorescence microscope.

Although the GFP-AR were diffusely distributed within the cytoplasm when the LNCaP cells were transfected with GFP-AR, when treated with dihydrotestosterone ($10^{-7}$M), the GFP-AR rapidly translocated into the nucleus and formed foci (dots) (FIG. 1). On the other hand, when treated with the compound of formula (Ia) ($10^{-5}$ M), although GFP-AR translocated into the nucleus, clear foci (dots) were not formed, but rather demonstrated a diffuse distribution pattern in the nucleus (FIG. 2).

Figure 3:
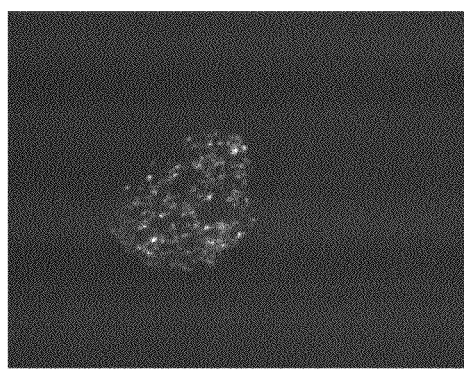
FIG. 3 is an image of an NIH-3T3-L1 cell transfected with AR-GFP followed by treatment with $10^{-7}$ M dihydrotestosterone as observed with a confocal laser fluorescence microscope.
Figure 4:
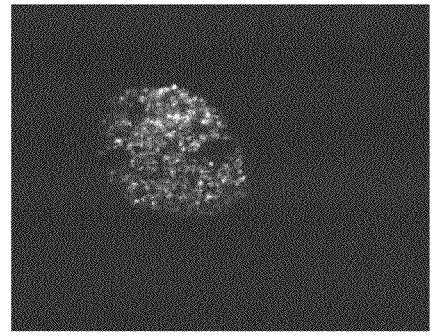
FIG. 4 is an image of an NIH-3T3-L1 cells transfected with AR-GFP followed by treatment with a compound represented by formula (I) at $10^{-5}$ M as observed with a confocal laser fluorescence microscope.

Moreover, a similar experiment was also conducted on NIH-3T3-L1 cells transfected with GFP-AR. In this case, both dihydrotestosterone ($10^{-7}$ M) and the compound of formula (Ia) ($10^{-5}$ M) transfered GFP-AR into the nucleus, and formed the subnuclear foci (dots) (FIGS. 3 and 4).

According to this experiment, although both dihydrotestosterone and the compound of formula (Ia) exhibited the ligand binding and demonstrated the different behavior in LNCaP cells, they behaved similarly in NIH-3T3-L1 preadipocytes, and the activities of these AR ligands on expression of PSA or UCP-1 were determined to not be the same.

Furthermore, GFP fluorescence was excited using a laser light having a wavelength of 488 nm from an air-cooled, fiber-coupled argon laser for the purpose of carrying out single fluorescent protein imaging. Although it is necessary to match the expression levels of transfected proteins in order to observe the theoretical intracellular interactions, when co-transfection was carried out, the amount of each AR-GFP plasmid was equal on a molar basis. Cells in which expression level of the target protein was suitable were selected microscopically. LSM images were exported as TIF files, and final images were generated using Adobe Illustrator and Adobe Photoshop (Adobe Systems).

(4) Study on Virilization Effect of Compounds:

The virilization effect of compounds was studied by using the changes in prostate weight during administration of the compounds to ORX rats as an indicator of virilization effect.

1) Rat Processing 11-week-old, male Sprague-Dawley (SD) rats (320 to 340 g, purchased from Charles River Japan) were housed for 1 week in a room maintained at a light-dark cycle of 12 hours per day and controlled at a set temperature and humidity while allowing free access to a commercially available standard rodent diet and water.

After housing the animals, the animals were anesthetized with ether, and underwent bilateral orchiectomy (orchiectomized rats: ORX) or a sham treatment. After awaking from the anesthesia, the animals were assigned to test groups of 3 to 5 animals each. Starting on the day after surgery, the animals were subcutaneously injected once a day with an injection solution of the test compound (prepared by dissolving the test compound in a small amount of DMSO and diluting with olive oil for animal testing (consisting of 95% olive oil and 5% DMSO)) at the rate of 0.1 ml/100 g of body weight. After 21 days, the rats were sacrificed by exsanguination from the abdominal artery, the ventral prostates and anal levator muscle were excised and weighed followed by immersing in RNAlater (Nacalai Tesque) for extraction of RNA. In addition, soft tissue was removed from the right femur, and immersed in 75% ethanol followed by storage for subsequent measurement of the bone mineral density. Moreover, liver and visceral fat tissue were collected and immersed in RNAlater for RNA extraction.

2) Changes in Prostate Weight

The prostate weights of the animals that were measured in the manner described above are shown in the following Table 4.

TABLE 4

Prostate Weights (mg/100 g of body weight)

|  | Dose of test compound | |
|---|---|---|
|  | 1 mg/Kg | 10 mg/Kg |
| Control (solvent administration) | 10.2** | |
| Dihydrotestosterone | 168.6**,## | 216.9*,## |
| Compound of formula (Ia) | 11.1** | 13.3** |
| Sham treatment | 132.5 | |

*p < 0.05 (versus sham),
**p < 0.01 (versus sham),
p < 0.01 (versus solvent administration)

Although the prostate weight decreased dramatically following orchiectomy in comparison with the sham treatment group, it increased dose-dependently in the case of administration of dihydrotestosterone. However, the prostate weights of rats administered with the compound of formula (Ia) did not increase at doses of 1 to 10 mg/kg body weight, thus indicating that the compound of formula (Ia) does not demonstrate virilization effect in the manner of dihydrotestosterone.

Moreover, PSA mRNA expression levels in the prostates of the ORX rats were also measured during administration of the test compound in the manner described below.

3) Real-Time PCR for Measuring Tissue mRNA

Total RNA in various tissues of the ORX rats was isolated using the RNeasy Mini Kit or RNeasy Fibrous Tissue Mini Kit (Qiagen). 1 µg of this total RNA was subjected to reverse transcription using the QuantiaTect Reverse Transcription Kit (Qiagen). Next, cDNA was subjected to real-time PCR analysis using LightCycler (Roche Diagnostics) and each of the transcription products was quantified. Furthermore, PCR was carried out in 20 µl of a reaction mixture under the following conditions using SYBR Premix Ex Taq (Takara Biotechnology): 50 cycles consisting of denaturation for 5 seconds at 95° C., annealing for 20 seconds at 60° C. and elongation for 25 seconds at 72° C. In addition, glyceraldehyde-3-phosphate dehydrogenase (GAPDH) mRNA was simultaneously amplified as an internal standard, and the real-time PCR value of each transcription product were calculated as a relative value based on GAPDH. The sequences of the forward and reverse primers for each target transcription product are shown in the following Table 5.

TABLE 5

Sequences of Forward and Reverse Primers for Each Target Transcription Product

| Target | Forward | Reverse | Size (bp) |
|---|---|---|---|
| PSA | AGGTGACAGATC TCATGCTGTGTG (SEQ ID NO: 9) | TGGCTGGCAT ATTGGGTTCA (SEQ ID NO: 10) | 153 |
| PPARδ | CCCAAGTTCGA GTTTGCTGTCA (SEQ ID NO: 11) | TCCACCTGTG GCACGTTCA (SEQ ID NO: 12) | 125 |
| GAPDH | GGCACAGTCAA GGCTGAGAATG (SEQ ID NO: 13) | ATGGTGGTGAA GACGCCAGTA (SEQ ID NO: 14) | 143 |

TABLE 5-continued

Sequences of Forward and Reverse Primers
for Each Target Transcription Product

| Target | Forward | Reverse | Size (bp) |
|---|---|---|---|
| SREBP-1c | GCGCGGA CGACGGA (SEQ ID NO: 15) | AGTCACTGTCTTG GTTGTTGATGAG (SEQ ID NO: 16) | 72 |
| FAS | GCGGGCGTG GTAATGCT (SEQ ID NO: 17) | CTGTTCGCAAA TACGCTCCAT (SEQ ID NO: 18) | 71 |
| CPT-1 | ATTTTGGCGA CAGACTCAGG (SEQ ID NO: 19) | AGGGGCAGGA ATCAAACAAG (SEQ ID NO: 20) | |
| IRS-2 | TGAGACCAAG TGGCATCGTT (SEQ ID NO: 21) | CTCTTGGGCTC AGTGGGTAGA (SEQ ID NO: 22) | 142 |
| UCP-1 | TACCCAGCTGT GCAATGACCA (SEQ ID NO: 23) | GCACACAAACAT GATGACGTTCC (SEQ ID NO: 24) | 113 |

4) PSA mRNA Expression Levels in ORX Rat Prostates

The PSA mRNA expression levels in the prostates of the ORX rats obtained in the aforementioned section (4)-1) were measured according to the method of section (4)-3). Those results are shown in the following Table 6.

TABLE 6

PSA mRNA/GAPDH mRNA in Prostates

| | Dose of test compound | |
|---|---|---|
| | 1 mg/Kg | 10 mg/Kg |
| Control (solvent administration) | 1.0** | |
| Dihydrotestosterone | 211.4**,## | 209.8**,## |
| Compound of formula (Ia) | 1.0** | 1.2** |
| Sham treatment | 114.4 | |

**$p < 0.01$ (versus sham),
$p < 0.01$ (versus solvent administration)

Although PSA mRNA levels decreased dramatically following orchiectomy as compared with the sham treatment group, they increased about 1.8-fold in comparison with the sham treatment group due to administration of dihydrotestosterone. On the other hand, there were no changes observed in PSA mRNA levels in the group treated with the compound of formula (Ia).

According to the above results and the results obtained in section (4)-2), in contrast to the naturally-occurring AR ligand dihydrotestosterone, the compound of formula (Ia) was determined to not have hardly any virilization effect with respect to prostate weight and stimulation of PSA expression. Furthermore, there were no differences in body weight observed between any of the compound treatment groups. In addition, body weights gradually increased during the 3-week test period for all rats.

(5) Study on Anabolic Effect of Compounds:

The anabolic effect of compounds was studied by using as indicators changes in anal levator muscle weight and bone mineral density (BMD) of the femur and vertebra in the ORX rats treated in the aforementioned section (4)-1).

1) Changes in Anal Levator Muscle Weight

Anal levator muscle is a typical skeletal muscle localized around the rat rectum, and is considered to be sensitive to male steroid hormone. Although the anal levator muscle is considerably smaller in castrated rats as compared with normal male rats, its weight is well known to be able to be restored to normal by administration of androgen (J. Pharmacol. Exp. Ther., 91, 38-44). The results of measuring the weights of the anal levator muscle in the ORX rats obtained in section (4)-1) are shown in the following Table 7.

In addition, expression levels of peroxisome proliferator activating factor receptor-delta (PPARδ) mRNA in anal levator muscle were also measured. This is because this nuclear receptor has been indicated to be related to β-oxidation of fatty acids and energy consumption in skeletal muscle (Proc. Natl. Acad. Sci. USA, 100, 15924-15929). These results are also shown in Table 7. Furthermore, measurements were carried out using a similar method as that previously described.

TABLE 7

Anal Levator Muscle Weights (mg/100 g body weight) and PPARδ mRNA/GAPDH mRNA therein

| | Anal levator muscle weight | | PPARδ mRNA/GAPDH mRNA | |
|---|---|---|---|---|
| | Dose of test compound | | Dose of test compound | |
| | 1 mg/Kg | 10 mg/Kg | 1 mg/Kg | 10 mg/Kg |
| Control (solvent administration) | 41.6** | | 1.0 | |
| Dihydrotestosterone | 93.8## | 120.6**,## | 0.9 | 0.5 |
| Compound of formula (Ia) | 59.1 | 66.2* | 0.9 | 1.7* |
| Sham treatment | 73.1 | | 0.5 | |

*$p < 0.05$ (versus sham),
**$p < 0.01$ (versus sham),
$p < 0.01$ (versus solvent administration)

As was predicted, anal levator muscle weights decreased in comparison with the sham treatment group as a result of castration. This decrease was restored by administration of dihydrotestosterone at 1 and 10 mg/kg, and weights increased beyond those in the case of the sham treated rats. On the other hand, in the case of the compound of formula (Ia), anal levator muscle weights increased significantly to a similar level to that observed in the sham treatment group at a dose of 10 mg/kg. This result indicates that the compound of formula (Ia) has anabolic effect on muscle in the same manner as dihydrotestosterone in ORX rats.

In addition, although expression of PPARδ mRNA increased in anal levator muscle as a result of castration, dihydrotestosterone inhibited this expression dose-dependently. However, it is interesting to note that the compound of formula (Ia) enhanced this expression at 10 mg/kg.

2) Femoral and Vertebral Bone Density

BMD value of epiphyseal cancellous bone of the femur and vertebra of ORX rats treated in the aforementioned section (4)-1) were measured using Scan Xmate-A100S (Comscantecno). Those results are shown in the following Table 8.

TABLE 8

Femoral and Vertebral BMD (mg/cm³)

|  | Femur Dose of test compound | | | Vertebra Dose of test compound | | |
| --- | --- | --- | --- | --- | --- | --- |
|  | 1 mg/Kg | 10 mg/Kg | 30 mg/Kg | 1 mg/Kg | 10 mg/Kg | 30 mg/Kg |
| Control (solvent administration) |  | 465.3 |  |  | 762.7 |  |
| Dihydrotestosterone | 472.0 | 473.6 | — | 768.4 | 763.2 | — |
| Compound of formula (Ia) | 447.2 | 454.0 | 475.9 | 769.5 | 770.3 | 775.1 |
| Sham treatment |  | 517.1 |  |  | 770.8 |  |

Local conversion of testicular testosterone into estrogen is well known to contribute to maintaining bone mass. However, the direct effect on dihydrotestosterone-androgen receptor-based bone has also been clearly demonstrated from the fact that ARKO mice demonstrate bone loss due to increased bone resorption, while females do not (Proc. Natl. Acad. Sci., 100, 9416-9421).

Femoral BMD value decreased slightly from 517.1 mg/cm³ (sham) to 465.3 mg/cm³ due to castration. Although dihydrotestosterone increased this decreased value by castration to 473.6 mg/cm³ at a dose of 10 mg/kg, this recovery did not reach the level of the sham group. The compound of formula (Ia) also increased BMD value dose-dependently, and increased this value to 475.9 mg/cm³ at a dose of 30 mg/kg. However, this value was not statistically significant.

Vertebral BMD value decreased slightly from 770.8 mg/cm³ (sham) to 762.7 mg/cm³ due to castration. Although dihydrotestosterone did not have an effect on vertebral BMD, the compound of formula (Ia) tended to increase BMD value dose-dependently, and increased this value to 775.1 mg/cm³ at a dose of 30 mg/kg. However, this value was also not statistically significant.

Based on the above results and those described in section (5)-1), the compound of formula (Ia) was shown to have anabolic activating tendencies in the same manner as dihydrotestosterone in ORX rats.

(6) Measurement of Plasma Gonadotropin Levels:

Characteristics of the effect of compounds on the pituitary gland were investigated by measuring plasma concentrations of LH and FSH in ORX rats treated in the aforementioned section (4)-1). The measurement results are shown in the following Table 9.

feedback mechanism that has been adequately elucidated with respect to the hypothalamus-pituitary gland-reproductive glands, in contrast thereto, the compound of formula (Ia) did not inhibit LH levels, but rather increased LH levels dose-dependently.

Moreover, although FSH levels were inhibited to levels observed in the untreated control group by administration of dihydrotestosterone at a dose of 1 or 10 mg/kg, the compound of formula (Ia) did not have any effect on FSH at a dose of 1 or 10 mg/kg.

(7) Measurement of Plasma Adiponectin Levels:

Plasma testosterone levels were low in the ORX rats (≤0.1 ng/ml) and normal in the sham treatment group (1.275 ng/ml), thus indicating that the castration of rats was successful and that these results can be trusted.

Adiponectin which is a plasma protein originating from adipocytes, is present in abundance in the plasma, and has recently attracted considerable attention due to its insulin-sensitizing effect and antiatherogenic effect (Natl. Med., 8, 731-737; J. Biol. Chem., 278, 2461-2468; Biochem. Biophys. Res. Commun., 257, 79-83). Testosterone has been reported to inhibit secretion of adiponectin from adipocytes in humans and rats, and the castration has been reported to increase plasma adiponectin concentrations, in particular increase the concentrations of high molecular weight (HMW) adiponectinin in mice (J. Biol. Chem., 280(18), 18073-18080; J. Androl., 26, 85-92).

The inventors of the present invention measured total plasma adiponectin levels in ORX rats treated in the aforementioned section (4)-1). Plasma insulin levels were also measured simultaneously. Those results are shown in the following Table 10.

TABLE 9

Plasma LH and FSH Concentrations (ng/mL)

|  | LH Dose of test compound | | FSH Dose of test compound | |
| --- | --- | --- | --- | --- |
|  | 1 mg/Kg | 10 mg/Kg | 1 mg/Kg | 10 mg/Kg |
| Control (solvent administration) | 10.3* | | 44.1* | |
| Dihydrotestosterone | 0.8## | 1.0## | 9.3* | 5.1* |
| Compound of formula (Ia) | 12.6** | 19.9*,## | 48.7* | 46.3* |
| Sham treatment | 1.7 | | 12.1 | |

*p < 0.05 (versus sham),
**p < 0.01 (versus sham),
p < 0.01 (versus solvent administration)

Castration caused a considerable increase in LH and FSH levels in comparison with the sham treatment group. Although dihydrotestosterone inhibited LH levels by inhibiting secretion of gonadotropins from the pituitary gland by a

TABLE 10

Plasma Adiponectin and Insulin Concentrations (μg/mL)

|  | Adiponectin Dose of test compound | | Insulin Dose of test compound | |
| --- | --- | --- | --- | --- |
|  | 1 mg/Kg | 10 mg/Kg | 1 mg/Kg | 10 mg/Kg |
| Control (solvent administration) | 2.2* | | 1.0 | |
| Dihydrotestosterone | 1.4 | 1.4 | 5.1 | 4.9 |
| Compound of formula (Ia) | 2.2* | 2.1* | 1.5 | 2.9 |
| Sham treatment | 1.3 | | 1.6 | |

*p < 0.05 (versus sham)

Although the castration significantly increased the plasma adiponectin levels, this increase was inhibited to the level of the sham treatment rats by administration of dihydrotestosterone at 1 or 10 mg/kg. In contrast, the compound of formula (Ia) did not demonstrate such inhibitory activity on the adiponectin levels.

On the other hand, although dihydrotestosterone as well as the compound of formula (Ia) increased the insulin levels, this activity was milder in the group treated with the compound of formula (Ia). According to this result, the compound of formula (Ia) is suggested to have a greater activity of causing the high insulin sensitivity than dihydrotestosterone.

(8) Measurement of Plasma Triglyceride and Cholesterol Levels:

Plasma triglyceride and cholesterol levels were measured to characterize the metabolic profiles of ORX rats treated in the aforementioned section (4)-1). Those results are shown in the following Table 11.

TABLE 11

Plasma Triglyceride and Cholesterol Concentrations (mg/dL)

|  | Triglyceride Dose of test compound | | Cholesterol Dose of test compound | |
|---|---|---|---|---|
|  | 1 mg/Kg | 10 mg/Kg | 1 mg/Kg | 10 mg/Kg |
| Control (solvent administration) | 130.7 | | 78.0 | |
| Dihydrotestosterone | 201.8 | 226.2 | 62.4 | 56.2 |
| Compound of formula (Ia) | 41.3** | 39.3** | 66.0 | 71.5 |
| Sham treatment | 236.5 | | 64.8 | |

**$p < 0.01$ (versus sham)

Plasma triglyceride levels are normally determined according to the balance between the synthesis and the secretion of triglyceride-rich lipoproteins containing VLDL-triglycerides in the liver, and the clearance from blood vessels by peripheral lipoprotein lipases (LPL) that hydrolyze triglycerides in an insulin-dependent form. Consequently, although insulin resistance and its secondary disease of hyperinsulinism are frequently associated with hypertriglyceridemia, this disease state is caused by the promotion of VLDL-triglyceride synthesis in the liver mediated primarily by activation of SREBP-1c (Prog. Lipid. Res., 40, 439) and the accumulation of triglyceride-rich lipoproteins in the blood caused by a decrease in peripheral LPL activity.

In this test, dihydrotestosterone raised triglyceride levels and lowered cholesterol levels. On the other hand, the compound of formula (Ia) surprisingly lowered triglyceride levels considerably, but did not have an effect on cholesterol levels in contrast to the activity of dihydrotestosterone. This can be partially explained by the overall beneficial activity of the compound of formula (Ia) on insulin sensitivity.

(9) Measurement of SREBP-1c, FAS and CPT-1 mRNA Levels in Liver and Visceral Fat:

Expression of lipogenic genes in the liver and visceral fat is known to be controlled by multiple transcription factors, including sterol regulatory element binding protein 1c (SREBP-1c), that fulfill an essential role in lipid homeostasis control in animals. SREBP-1 c has been demonstrated to directly activate the expression of more than 30 genes involved in biosynthesis of cholesterol, fatty acids, triglycerides and phospholipids (J. Clin. Invest., 109, 1125-1131). Carnitine palmitoyl transferase 1 (CPT-1) is an important enzyme for carnitine-dependent transport across mitochondrial inner membranes, and a deficiency thereof causes a decrease in the rate of β oxidation of fatty acids. In addition, fatty acid synthase (FAS) is a fatty acid synthase targeted by SREBP-1c.

In order to investigate the mechanism of the triglyceride lowering activity of test compounds, mRNA levels of SREBP-1c, FAS and CPT-1 were measured in the liver and visceral fat of ORX rats treated in the aforementioned section (4)-1). In addition, mRNA levels of insulin receptor substrate 2 (IRS-2) in the liver were also measured. These results are shown in the following Tables 12 to 15.

TABLE 12

SREBP-1c mRNA/GAPDH mRNA Levels in Liver and Visceral Fat

|  | Liver Dose of test compound | | Visceral Fat Dose of test compound | |
|---|---|---|---|---|
|  | 1 mg/Kg | 10 mg/Kg | 1 mg/Kg | 10 mg/Kg |
| Control (solvent administration) | 0.7 | | 1.0 | |
| Dihydrotestosterone | 3.4 | 3.2 | 1.8 | 2.2 |
| Compound of formula (Ia) | 0.8 | 0.6 | 0.8 | 0.5 |
| Sham treatment | 1.0 | | 1.0 | |

TABLE 13

FAS mRNA/GAPDH mRNA Levels in Liver and Visceral Fat

|  | Liver Dose of test compound | | Visceral Fat Dose of test compound | |
|---|---|---|---|---|
|  | 1 mg/Kg | 10 mg/Kg | 1 mg/Kg | 10 mg/Kg |
| Control (solvent administration) | 0.9 | | 0.5 | |
| Dihydrotestosterone | 8.0 | 7.1 | 2.3 | 3.5*,# |
| Compound of formula (Ia) | 0.7 | 0.5 | 0.3* | 0.6 |
| Sham treatment | 1.0 | | 1.0 | |

*$p < 0.05$ (versus sham),
$p < 0.05$ (versus solvent administration)

TABLE 14

CPT-1 mRNA/GAPDH mRNA Levels in Liver and Visceral Fat

|  | Liver Dose of test compound | | Visceral Fat Dose of test compound | |
|---|---|---|---|---|
|  | 1 mg/Kg | 10 mg/Kg | 1 mg/Kg | 10 mg/Kg |
| Control (solvent administration) | 1.4 | | 1.7 | |
| Dihydrotestosterone | 1.3 | 0.4 | 1.7 | 0.8 |
| Compound of formula (Ia) | 3.2**,# | 4.2* | 2.0 | 2.6 |
| Sham treatment | 1.0 | | 1.0 | |

*$p < 0.05$ (versus sham),
**$p < 0.01$ (versus sham),
$p < 0.05$ (versus solvent administration)

TABLE 15

IRS-2 mRNA/GAPDH mRNA Levels in Rat Liver

|  | Dose of test compound | |
|---|---|---|
|  | 1 mg/Kg | 10 mg/Kg |
| Control (solvent administration) | 4.8 | |
| Dihydrotestosterone | 5.1 | 0.8 |
| Compound of formula (Ia) | 10.6** | 8.8* |
| Sham treatment | 1.0 | |

*$p < 0.05$ (versus sham),
**$p < 0.01$ (versus sham)

As can be seen in Tables 12 to 14 above, the similar results were obtained for both the liver and visceral fat. SREBP-1c mRNA levels of the group treated with the compound of formula (Ia) were lower in both tissues. FAS mRNA levels were also lower by treatment with the compound of formula (Ia) (Tables 12 and 13). Although the lipid formation is inhibited as a result, on the other hand, CPT-1 mRNA levels for the compound of formula (Ia) were higher in comparison with dihydrotestosterone (Table 14), and the decomposition of fat was more activated. In this mariner, the decreased expression of SREBP-1c and FAS and the increased expression of CPT-1 have the potential to be factors responsible for decreased plasma triglyceride levels attributable to treatment with the compound of formula (Ia).

Insulin receptor substrate refers to a group of proteins that are phosphorylated by activated insulin receptors, and IRS-2 is one of the nine members of this group (Nature, 377, 173-177). IRS-2 deficiencies in mouse hypothalamus and j3 cells have recently been indicated to cause the symptoms of type 2 diabetes (J. Clin. Invest., 114, 917-927). IRS-2 is also known to promote the growth and survival of $\beta$ cells (Nature, 391, 900-904).

As shown in Table 15 above, although the expression of a gene downstream from SREBP-1c in the liver, namely mRNA level of IRS-2, was increased by treatment with the compound of formula (Ia), it decreased by treatment with dihydrotestosterone. Inhibition of expression of SREBP-1c induced by the compound of formula (Ia) is thought to be intimately related to increased IRS-2 mRNA in the liver. In addition, the compound of formula (Ia) also has the possibility of demonstrating an insulin sensitizing effect in the liver through an up-regulation mechanism of this IRS-2.

Decreases in serum triglyceride levels caused by the compound of formula (Ia) can also be explained from the viewpoint of up-regulation of PPARδ in skeletal muscle. Activation of PPARδ causes up-regulation of genes associated with fatty acid oxidation in skeletal muscle, and uncoupling of mitochondria. Selective PPARδ agonists have been indicated to increase insulin sensitivity and prevent diet-induced obesity (Am. J. Physiol. Endocrinol. Metab., 293, E1256-E1264).

However, in the previously indicated Table 3, dihydrotestosterone and the compound of formula (Ia) were indicated to increase transcription levels of UCP-1 in NIH-3T3-L1 cells. Thus, UCP-1 mRNA levels in rat visceral fat were also measured for the purpose of confirmation. The measurement results are shown in the following Table 16.

TABLE 16

UCP-1 mRNA/GAPDH mRNA Levels in Rat Visceral Fat

| | Dose of test compound | |
|---|---|---|
| | 1 mg/Kg | 10 mg/Kg |
| Control (solvent administration) | 1.0 | |
| Dihydrotestosterone | 0.8 | 0.9 |
| Compound of formula (Ia) | 1.7 | 1.5 |
| Sham treatment | | 1.0 |

Although a trend was slightly observed in which the compound of formula (Ia) increased UCP-1 mRNA levels, this increase was not significant. In addition, dihydrotestosterone had hardly any effect on UCP-1 mRNA levels.

(10) Effect of Compounds on Accumulation of Visceral Fat 9-week-old B6 mice were divided into a control group, high-fat diet group and high-fat diet+compound of formula (Ia) group of 10 animals each, and housed and observed for 16 weeks. During this period, the compound of formula (Ia) was subcutaneously injected at 10 mg/kg every other day, body weights were measured once a week, and food intake was measured once every 4 weeks.

After 16 weeks, the body weights, bone mineral densities, fat distributions and exercise levels of the mice were measured, followed by collecting blood samples and finally sacrificing the animals and collecting their organs. The average value of body weight, serum glucose concentration and serum insulin concentration of each group after 16 weeks are shown in the following Table 17.

TABLE 17

Average Value of Body Weight, Serum Glucose Concentration and Serum Insulin Concentration

| | Body weight (g) | Serum glucose concentration (mg/dL) | Serum insulin concentration (ng/mL) |
|---|---|---|---|
| Control (ordinary diet) | 30.7 | 75 | 0.13 |
| High-fat diet | 36.6 | 113.2** | 0.46** |
| High-fat diet + compound of formula (Ia) | 34.9### | 82.2## | 0.27# |

**$p < 0.01$ (versus ordinary diet),
$p < 0.05$ (versus high-fat diet),
$p < 0.01$ (versus high-fat diet),
$p = 0.237$ (versus high-fat diet)

First, with respect to body weight, body weights in the high-fat diet+compound of formula (Ia) group were significantly lower than in the high-fat diet group. On the basis of this result, the compound of formula (Ia) was suggested to have the effect of inhibiting the weight gain. Furthermore, the changes in average value of food intake in each group are shown in the following Table 18. There were no significant differences in food intake in each of the groups.

TABLE 18

Changes in Food Intake in Each Group (g/day)

| | Week 4 | Week 8 | Week 12 | Week 16 |
|---|---|---|---|---|
| Control (ordinary diet) | 2.85 | 2.85 | 2.76 | 3.21 |
| High- fat diet | 2.36 | 2.51 | 2.40 | 3.17 |
| High- fat diet + compound of formula (Ia) | 2.11 | 2.01 | 2.22 | 2.34 |

Next, with respect to serum glucose and serum insulin concentrations, the increasing due to the high-fat diet were significantly inhibited by the compound of formula (Ia). Inhibition of increasing these values is effective for preventing and/or treating lifestyle-related diseases such as diabetes.

In addition, glucose tolerance tests were also carried out on the mice after housing for 16 weeks. The mice were divided into groups of 5 mice each, injected at 1 g/kg, and glucose value was then measured over time. The results are shown in the following Table 19.

TABLE 19

Changes in Glucose Value in a Mouse Glucose Tolerance Test (mg/dL)

| | Time after injection (min) | | | | | |
|---|---|---|---|---|---|---|
| | 0 | 15 | 30 | 60 | 90 | 120 |
| Control (ordinary diet) | 75 | 269.2 | 271.8 | 176.4 | 153.4 | 108.6 |
| High-fat diet | 113.2** | 298.4 | 340.2* | 297.8* | 316.6** | 219.0** |
| High-fat diet + compound of formula (Ia) | 82.2## | 293.6 | 327.6* | 249.4 | 262.0* | 163.0 |

*$p < 0.05$ (versus ordinary diet),
**$p < 0.01$ (versus ordinary diet),
$p < 0.01$ (versus high-fat diet)

Figure 5:
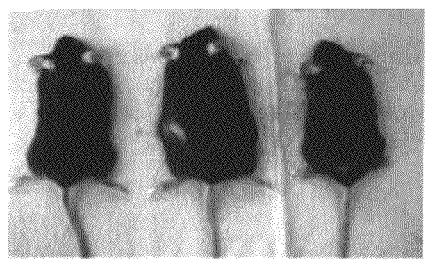
FIG. 5 shows photographs of the appearances of mice of a control group, high-fat diet group and high-fat diet+compound of formula (Ia) group when 9-week-old B6 mice were administered a high-fat diet or a high-fat diet+compound represented by formula (Ia) for 16 weeks (left: control group, center: high-fat diet group, right: high-fat diet+compound of formula (Ia) group).

However, the weight gain inhibitory effect as described above typically appears in the appearance of the mice of each group after 16 weeks. Although FIG. 5 shows photographs of mice from each group arranged in a row after 16 weeks, the mouse of the high-fat diet+compound of formula (Ia) group (right) exhibits an appearance that more closely resembles the rat from the ordinary diet group (left) than the rat from the high-fat diet group (center).

Figure 6:
FIG. 6 shows photographs of the visceral fat of mice of a control group, high-fat diet group and high-fat diet+compound of formula (Ia) group when 9-week-old B6 mice were administered a high-fat diet or a high-fat diet+a compound represented by formula (Ia) for 16 weeks (left: control group, center: high-fat diet group, right: high-fat diet+compound of formula (Ia) group).

However, it was surprisingly found that, as shown in FIG. 6, a prominent difference in accumulation of visceral fat was observed between the high-fat diet group and the high-fat diet+compound of formula (Ia) group. Namely, although visceral fat increased prominently in the animal of the high-fat diet group (center), visceral fat in the high-fat diet+compound of formula (Ia) group (right) was roughly the same as that of the rat of the ordinary diet group (left). Thus, the compound of formula (Ia) was clearly demonstrated to have a prominent effect of inhibiting increases in visceral fat.

As was previously described, the SARM of the present invention has an effect that promotes muscle development, inhibits accumulation of visceral fat, and enhances insulin sensitivity in the liver, adipose tissue and muscle without stimulating the prostate gland or inhibiting the hypothalamus-pituitary gland-reproductive glands. Since enhanced insulin sensitivity and decreased triglycerides are essential targets for treatment or prevention of diabetes and atherosclerosis (Circulation, 100, 475-482), the SARM of the present invention is expected to be used as a promising prophylactic and/or therapeutic agents for lifestyle-related diseases.

The SARM of the present invention can be used by formulating into various drug forms such as solid forms (for example, tablets, hard capsules, soft capsules, granules, grains, pills or lozenges, etc.), semi-solid forms (for example, suppositories or ointments, etc.) or liquid forms (for example, injection preparations, emulsions, suspensions, lotions or sprays, etc.) together with non-toxic additives. Examples of non-toxic additives that can be used in the aforementioned formulations include starch, gelatin, glucose, lactose, fructose, maltose, magnesium carbonate, talc, magnesium stearate, methyl cellulose, carboxymethyl cellulose or salt thereof, gum arabic, polyethylene glycol, p-hydroxybenzoic acid alkyl ester, syrup, ethanol, propylene glycol, vaseline, carbowax, glycerin, sodium chloride, sodium sulfite, sodium phosphate and citric acid, etc. These formulations can also contain other therapeutically useful drugs.

Although varying depending to the drug form, the administration form and the like, the content of a compound having a selective androgen receptor modulatory activity in these formulations can typically be 0.1 to 50% by weight in the case of a solid or semi-solid form, and a concentration of 0.05 to 10% by weight in the case of a liquid form.

In addition, although varying over a wide range depending to the type of interested human or other warm-blooded animal, the type of interested disease, administration route, severity of symptoms or diagnosis of a physician and the like, the dose of a compound having a selective androgen receptor modulatory activity in the present invention can typically be within the range of 0.01 to 5 mg/kg per day, and preferably within the range of 0.02 to 2 mg/kg per day. However, a dose below the lower limit or above the upper limit of the aforementioned ranges can naturally also be administered corresponding to the severity of patient symptoms, physician's diagnosis and the like as described above. The above dose can be administered in a single administration or divided several administrations per day.

EXAMPLES

The following provides a more detailed explanation of the present invention through examples and formulation examples.

Example 1

Synthesis of 16a-homo-16a-oxestra-5-ene-3β-methoxide (compound of formula (IIIa)):

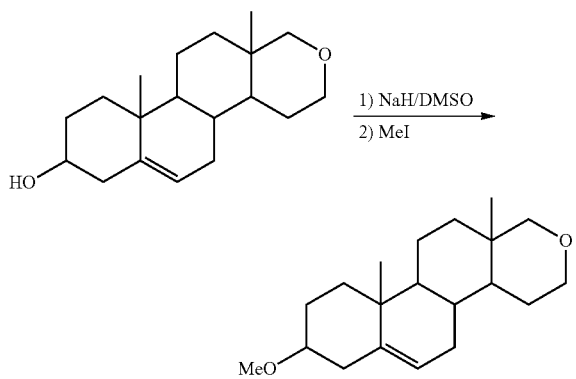

50 mg of 40% sodium hydride were washed wice with 3 ml of benzene followed by the addition of 0.5 ml of DMSO and stirring for 30 minutes at room temperature. 0.5 ml of DMSO solution containing 50 mg of the 3-OH form were dropped therein followed by stirring for 30 minutes. After adding 0.2 ml of methyl iodide and stirring for 15 minutes, ice water was added followed by extraction with ethyl acetate, washing with saturated brine and water, drying with anhydrous sodium sulfate and distilling off the ethyl acetate under reduced pressure. The residue was purified by thin layer chromatography (developing solvent: chloroform) to obtain 38.9 mg of the titled compound.

$^1$H-NMR (CDCl$_3$, δ): 0.94-1.09 (4H,m), 0.998 (3H,s), 1.001 (3H,s), 1.27 (1H,dt,J=12.7, 3.4 Hz), 1.32-1.62 (7H,m), 1.85-1.97 (2H,m), 2.03-2.20 (2H,m), 2.40 (1H,ddd,J-2.3, 4.6, 13.1 Hz), 2.98 (1H,d,J=10.8 Hz), 3.01-3.12 (1H,m), 3.33-3.42 (2H,m), 3.36 (3H,s), 4.02-4.08 (1H,m), 5.34-5.39 (1H, m)

MS (m/z): 304 (M$^+$)

Example 2

Formulation Example 1: Tablets

| | mg/tablet |
|---|---|
| Active ingredient | 5.0 |
| Starch | 10.0 |
| Lactose | 73.0 |
| Calcium carboxymethyl cellulose | 10.0 |
| Talc | 1.0 |
| Magnesium stearate | 1.0 |
| | 100.0 |

The active ingredient was crushed to a particle size of 70 μm or less followed by the addition of the starch, lactose and calcium carboxymethyl cellulose and mixing well. 10% starch paste was added to the mixed powder followed by stirring and mixing to produce granules. After drying, the particle size was granulated to about 100 μm followed by mixing with the talc and magnesium stearate and forming into tablets.

The invention claimed is:

1. A selective androgen receptor modulator, comprising as an active ingredient thereof a compound of the following formula (IIIa):

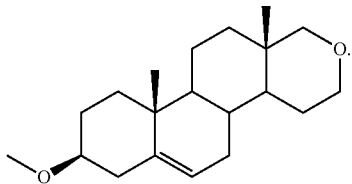

(IIIa)

2. A compound of the following formula

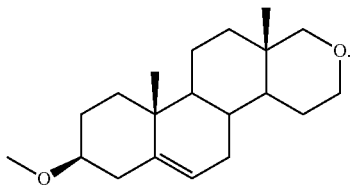

(IIIa)

3. A composition for treating a lifestyle-related disease comprising the selective androgen receptor modulator according to claim 1 and a non-toxic additive.

4. A composition for treating a lifestyle-related disease according to claim 3, wherein the lifestyle-related disease is at least one disease selected from the group consisting of obesity, insulin-resistant (type 2) diabetes, hyperlipemia and hypertension.

5. A method for treating a lifestyle-related disease comprising administering to a human a pharmaceutically effective amount of the selective androgen receptor modulator according to claim 1, wherein the lifestyle-related disease is at least one disease selected from the group consisting of obesity, insulin-resistant (type 2) diabetes, hyperlipemia (excluding familial hyperlipemia), hypertension, hyperuricemia, cardiovascular disease (excluding congenital cardiovascular diseases), colorectal cancer (excluding familial colorectal cancer), pulmonary squamous cell carcinoma, chronic bronchitis, emphysema, alcoholic liver disease, osteoporosis and periodontitis.

6. The composition for treating a lifestyle-related disease according to claim 3, wherein the lifestyle-related disease is at least one disease selected from the group consisting of obesity, insulin-resistant (type 2) diabetes, hyperlipemia (excluding familial hyperlipemia), hypertension, hyperuricemia, cardiovascular disease (excluding congenital cardiovascular diseases), colorectal cancer (excluding familial colorectal cancer), pulmonary squamous cell carcinoma, chronic bronchitis, emphysema, alcoholic liver disease, osteoporosis and periodontitis.

7. The method according to claim 5, wherein the lifestyle-related disease is at least one disease selected from the group consisting of obesity, insulin-resistant (type 2) diabetes, hyperlipemia (excluding familial hyperlipemia) and hypertension.

* * * * *